United States Patent
MacDougall et al.

(10) Patent No.: US 8,236,952 B2
(45) Date of Patent: Aug. 7, 2012

(54) PREPARATIONS CONTAINING AMINO ACIDS AND OROTIC ACID

(75) Inventors: Joseph MacDougall, Mississauga (CA); Shan Chaudhuri, Brampton (CA)

(73) Assignee: Northern Innovations Holding Corp., Oakville (CA)

( * ) Notice: Subject to any disclaimer, the term of this patent is extended or adjusted under 35 U.S.C. 154(b) by 1266 days.

(21) Appl. No.: 11/958,747

(22) Filed: Dec. 18, 2007

(65) Prior Publication Data
US 2009/0156812 A1    Jun. 18, 2009

(51) Int. Cl.
*C07D 239/557*    (2006.01)
(52) U.S. Cl. .................... 544/309; 544/311
(58) Field of Classification Search ............. 544/309, 544/311
See application file for complete search history.

(56) References Cited

U.S. PATENT DOCUMENTS

| | | | |
|---|---|---|---|
| 4,400,508 A | 8/1983 | Fukui et al. | |
| 2004/0033981 A1 | 2/2004 | von Borstel et al. | |
| 2004/0198823 A1 | 10/2004 | Abraham et al. | |
| 2005/0250674 A1 | 11/2005 | Amato | |

FOREIGN PATENT DOCUMENTS

| FR | 1980 M | 8/1963 |
|---|---|---|
| RU | 2086543 | 8/1997 |

OTHER PUBLICATIONS

Vigneron, CAPLUS Abstract 60:17223 (1964).*
Visek WJ. Nitrogen-stimulated orotic acid synthesis and nucleotide imbalance. Cancer Res. Apr. 1, 1992;52(7):2082s-4s.
Rosenfeldt FL. Editorial: Metabolic supplementation with orotic acid and magnesium orotate. Cardiovasc Drugs Ther. Apr. 1998;12(Suppl 2):147-52.
Classen HG. Magnesium orotate—experimental and clinical evidence. Rom J Intern Med. 2004;42(3):491-501.
Solomons G, et al. Organic Chemistry: Seventh Edition Upgrade. 2002. p. 840. John Wiley & Sons, Inc. Toronto, Canada.
Rennie MJ. Body maintenance and repair: how food and exercise keep the musculoskeletal system in good shape. Exp Physiol. Jul. 2005;90(4):427-36.
Smith K, et al. Effects of flooding amino acids on incorporation of labeled amino acids in human muscle protein. Am J Physiol. Jul. 1998;275(1 Pt 1):E73-8.
Matthews DE. Observations of branched-chain amino acid administration in humans. J Nutr. Jun. 2005;135(6 Suppl):1580S-4S.
French DN, et al. Anticipatory reponses of catecholamines on muscle force production. J Appl Physiol. Jan. 2007;102(1):94-102.
Barbul A. Arginine: biochemistry, physiology, and therapeutic implications. JPEN J Parenter Enteral Nutr. Mar.-Apr. 1986;10(2):227-38.
Appleton J. Arginine: Clinical potential of a semi-essential amino acid. Altern Med Rev. Dec. 2002;7(6):512-22.
Campbell BA, et al. The ergogenic potential of arginine. J Inter Soc Sports Nutri. 2004;1(2):35-8.
Mathias LJ, et al. Polydepsipeptides. 6. Synthesis of sequential polymers containing varying ratios of L-Alanine and L-Lactic aci. Macromolecules. May-Jun. 1978;11(3):534-9.
"4-DMAP (4-Dimethylaminopyridine)", Aldrich Technical Bulletin, AL-114, 4 pages, 1994.
Ragnarsson et al., "Novel Amine Chemistry Based on DMAP-Catalyzed Acylation", Acc. Chem. Res. 1998, 31(8), 494-501.
International Search Report for PCT/CA2007/002309.

* cited by examiner

*Primary Examiner* — Deepak Rao

(57) ABSTRACT

The present invention describes compounds produced from an orotic acid molecule and an amino acid molecule. The compounds being in the form of amino acid orotate compounds bound by an amide linkage and produced by one of two disclosed methods; 1) reacting orotic acid or derivatives thereof with a thionyl halide, and then combining the acyl halide with an amino acid in the presence of dichloromethane and a DMAP catalyst; or 2) protecting the carboxylic acid of an amino acid and then combining the amino acid with a DCC activated orotic acid, followed by removal of the carboxylic acid protecting group. The resulting amino acid orotate amide has an enhanced stability in solution as compared to a related ester. In addition, specific benefits are conferred by the particular amino acid used to form the compounds in addition to, and separate from, the orotate substituent.

22 Claims, No Drawings

PREPARATIONS CONTAINING AMINO ACIDS AND OROTIC ACID

FIELD OF THE INVENTION

The present invention relates to structures and methods for producing amino acid orotate amides. Specifically, the present invention relates to a compound comprising an orotic acid molecule bound to an amino acid. The amino acid is preferably a branched-chain amino acid and is bound to the orotate molecule via an amide linkage.

BACKGROUND OF THE INVENTION

Orotic acid, also known as pyrimidinecarboxylic acid, was historically believed to be a vitamin, i.e. vitamin B13; however, this is now understood to be incorrect. Orotic acid has a number of important roles in the body, including; acting as a key intermediate for the production of pyrimidines (Visek W J. Nitrogen-stimulated orotic acid synthesis and nucleotide imbalance. Cancer Res. Apr. 1, 1992; 52(7):2082s-4s), neutralizing excess ribose, and ensuring that adequate levels of beta-alanine, carnosine and anserine are present.

Supplementation with orotic acid and derivatives of orotate, particularly insoluble organic salts such as magnesium orotate, have been shown to successfully increase athletes' tolerance to extended periods of physical exertion (Rosenfeldt F L. Editorial: Metabolic supplementation with orotic acid and magnesium orotate. Cardiovasc Drugs Ther. April 1998; 12(Suppl 2):147-52). The increased tolerance to exercise observed with administration of orotic acid has been attributed to the acid's ability to improve the energy status of cells (Classen H G. Magnesium orotate-experimental and clinical evidence. Rom J Intern Med. 2004; 42(3):491-501), by stimulating the synthesis of glycogen and adenosine triphosphate (ATP).

The production of derivatives of orotic acid have been described in U.S. Pat. No. 4,400,508. This reference purports to describe alkyl, allyl, cyclohexyl, and benzyl derivatives of orotate, wherein the orotate is derivatized at one of the nitrogens present in the orotate.

U.S. Publication No. 2004/0033981 purports to describe pyrimidine precursors. The pyrimidine precursors are based upon orotate having one of three pyrimidines bound to nitrogen of the orotate ring. Additionally, this application discloses alcohol based esters of orotate, as well as salts of orotate.

U.S. Publication No. 2005/0250674 purports to describe creatine-orotate complexes and orotic acid derivatives. The creatine-orotate complexes are based on the formation of an anhydride bond between the carboxylic acids of both the creatine and the orotate. The orotic acid derivatives described are esters formed at the carboxylic acid of the orotate.

The above disclosed patents and applications recite orotate salts, esters, methods of synthesis, and uses thereof. However, the disclosed patents or applications fail to teach, suggest or disclose a compound comprising an orotate molecule bound to an amino acid via an amide bond. It is commonly known that hydrolysis of amides is more difficult to accomplish then the hydrolysis of esters (Solomons G, Fryhle C. Organic Chemistry: Seventh Edition Upgrade. 2002. pg 840. John Wiley & Sons, Inc. Toronto, Canada). Therefore, an amide of orotate and an amino acid is more stable in solution then the related ester.

Exercise is a major stimulus for skeletal muscle growth. During the hours following exercise, there are dynamic changes in the rates of both skeletal muscle synthesis and breakdown. The consumption of specific dietary components is known to further influence the response of skeletal muscle to exercise. The main component of food that is known to stimulate increased muscle protein synthesis is amino acids (Rennie M J. Body maintenance and repair: how food and exercise keep the musculoskeletal system in good shape. Exp Physiol. July 2005; 90(4):427-36). Increased levels of circulating essential amino acids have been shown to stimulate protein synthesis (Smith K, Reynolds N, Downie S, Patel A, Rennie M J. Effects of flooding amino acids on incorporation of labeled amino acids into human muscle protein. Am J Physiol. July 1998; 275(1 Pt 1):E73-8).

The branched-chain amino acids (BCAAs): Leucine, Isoleucine and Valine, are one group of amino acids that are commonly administered during and after exercise. BCAAs are considered essential amino acids since humans are unable to synthesis them—they must be obtained from the diet—despite their importance. These BCAAs are not only used in the synthesis of other amino acids, but are also important in the cell signal regulation of the anabolic process in skeletal muscle. BCAAs also increase the rate of protein synthesis as well as inhibiting protein degradation (Matthews D E. Observations of branched-chain amino acid administration in humans. J Nutr. June 2005; 135(6 Suppl):1580S-4S).

Additionally, other amino acids, such as Phenylalanine and Arginine are often supplemented during periods of exercise in order to make up for a deficiency or shortage of that amino acid as a result of depletion during periods of strenuous exercise.

The amino acid Phenylalanine is an essential amino acid, which can be converted into L-tyrosine and then into L-DOPA, which is further converted into one of three catecholamines: dopamine, norepinephrine and epinephrine. Increased levels of catecholamines induce a multitude of metabolic, hemodynamic and systemic effects (French D N, Kraemer W J, Volek J S, Spiering B A, Judelson D A, Hoffman J R, Maresh C M. Anticipatory responses of catecholamines on muscle force production. J Appl Physiol. January 2007; 102(1):94-102). A non-exhaustive list of these physiological responses include; promotion of energy availability to support the force-requiring demands of high-intensity resistance exercise, facilitation of the contractile characteristics of skeletal muscle, and redirection of blood flow to areas of the body where larger amounts are required at a given time.

Arginine is considered to be a semi-essential amino acid as it is normally synthesized in sufficient amounts by the body. However, conditions and circumstances are known wherein additional Arginine is required or desired, during exercise, for example. Arginine is known to participate in several important metabolic processes (Barbul A. Arginine: biochemistry, physiology, and therapeutic implications. JPEN J Parenter Enteral Nutr. March-April 1986; 10(2):227-38), such as acting as a precursor for the synthesis of proteins, other amino acids, urea, creatine and is a substrate involved in the synthesis of nitric oxide (NO) (Appleton J. Arginine: Clinical potential of a semi-essential amino. Altern Med Rev. December 2002; 7(6):512-22), and the detoxification of ammonia formed by amino acid catabolism (Campbell B A, La Bounty P M, Roberts M. The ergogenic potential of Arginine. J Inter Soc Sports Nutri. 2004; 1(2):35-8).

While the above referenced orotate compounds have attempted to address issues such as stability and solubility in addition to, and in some cases, attempting to add increased functionality as compared to orotate alone, no description has been made of any amino acid orotate compound united through an amide bond, thereby providing improved stability of the resultant molecule in solution as compared to corresponding esters.

SUMMARY OF THE INVENTION

In the present invention, compounds and methods of production are disclosed, wherein the compounds comprise a molecule of orotic acid bound to an amino acid, via an amide linkage, and having structures corresponding to the general Formula 1:

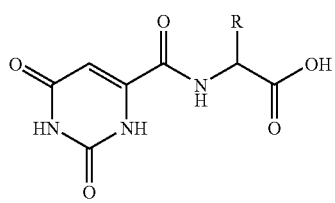

Formula 1 wherein:
R is selected from the group consisting of $(CH_3)_2CHCH_2$—; $(CH_3)_2CH$—; $CH_3CH_2CH(CH_3)$—; $H_2NC(=NH)NH(CH_2)_3$—; and $C_6H_5CH_2$—.

An additional aspect of the present invention discloses methods for producing the compounds having structures corresponding to Formula 1.

DETAILED DESCRIPTION OF THE INVENTION

In the following description, for the purposes of explanation, numerous specific details are set forth in order to provide a thorough understanding of the present invention. It will be apparent, however, to one skilled in the art that the present invention may be practiced without these specific details.

The present invention relates to routes of syntheses for amino acid orotate amides. In addition, specific benefits are conferred by the particular amino acid used to form the compounds in addition to, and separate from, the orotate substituent.

As used herein, 'orotic acid' refers to the chemical 6-carboxy-2,4-dihydroxypyrimidine, (CAS Registry No. 65-86-1), also known as, orotate, pyrimidinecarboxylic acid, vitamin B13, Uracil-6-carboxylic acid, 1,2,3,6-tetrahydro-2,6-dioxo-4-pyrimidinecarboxylic acid, whey factor, animal galactose factor, Oropur, or Orotyl. Additionally, as used herein, 'orotic acid' also includes derivatives of orotic acid such as amides and salts, as well as other derivatives, including derivatives having substantially similar pharmacoproperties to orotic acid upon metabolism to an active form.

According to the present invention, the compounds disclosed herein comprise an orotic acid molecule bound to an amino acid, wherein the amino acid is preferably a branched-chain amino acid. Furthermore, the orotic acid and amino acid, bound by an amide linkage have a structure according to Formula 1. The aforementioned compound being prepared according to the reaction as set forth for the purposes of the description in Scheme 1 below:

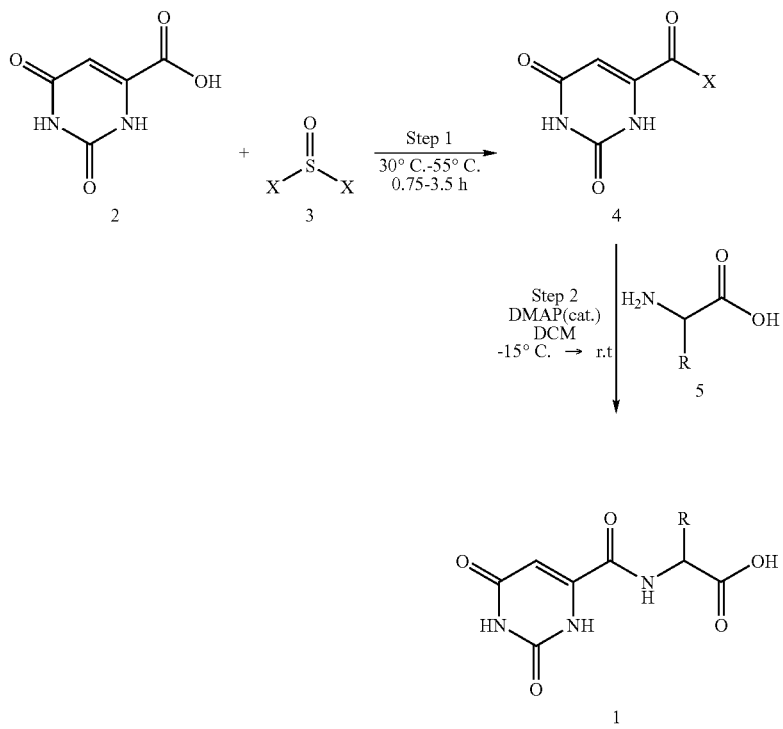

With reference to Scheme 1, in Step 1 an acyl halide (4) is produced via reaction of orotic acid (2) with at least an equivalent molar amount of thionyl halide (3).

In various embodiments of the present invention, the thionyl halide of (3) is selected from the group consisting of fluorine, chlorine, bromine, and iodine, the preferred method using chlorine or bromine.

The above reaction proceeds under conditions of heat ranging between from about 30° C. to about 55° C. and stirring over a period from about 0.75 hours to about 3.5 hours during which time the gases, sulfur dioxide and acidic gas, wherein the acidic gas species is dependent on the species of thionyl halide employed, are evolved. Preferably, the reactions proceed at about 45° C. for about 2 hours.

Step 2 describes the addition of the prepared acyl halide (4) to a suspension of an amino acid (5) in dichloromethane (DCM), in the presence of catalytic 4-dimethyl-aminopyridine (DMAP), to form the desired amino acid orotate amide (1). The addition of the acyl halide takes place at temperatures between about −15° C. and about 0° C. and with vigorous stirring. Following the complete addition of the acyl halide the reaction continues to stir and is allowed to subsequently warm to room temperature before the reaction mixture is filtered and then concentrated in vacuo and then purified by flash chromatography through a silica gel (SiO$_2$) packed column, yielding the target amide compound, amino acid orotate amide (1).

In various embodiments of the present invention, the amino acid (5) is selected from the group preferably consisting of Leucine, Valine, Isoleucine, Arginine and Phenylalanine. However any amino acid, as is known by one of skill in the art, may be utilized to synthesize an amino acid oratate amide according to the methods disclosed herein.

In a further embodiment of the present invention, the amino acid orotate amides disclosed herein may also be prepared according to the reaction as set forth for the purposes of the description in Scheme 2 below:

Scheme 2

Step 1:

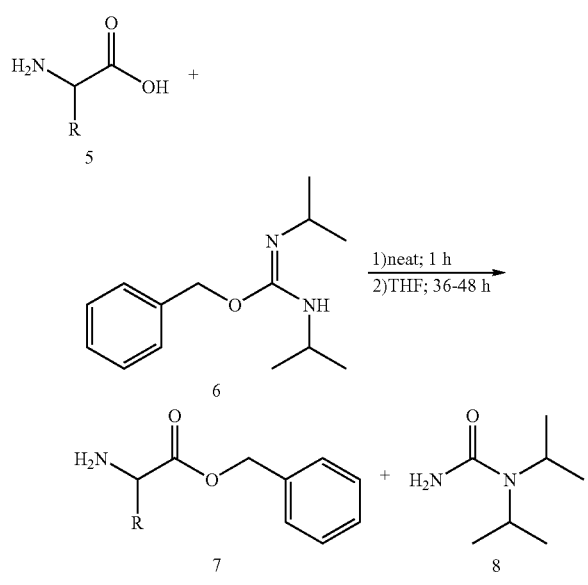

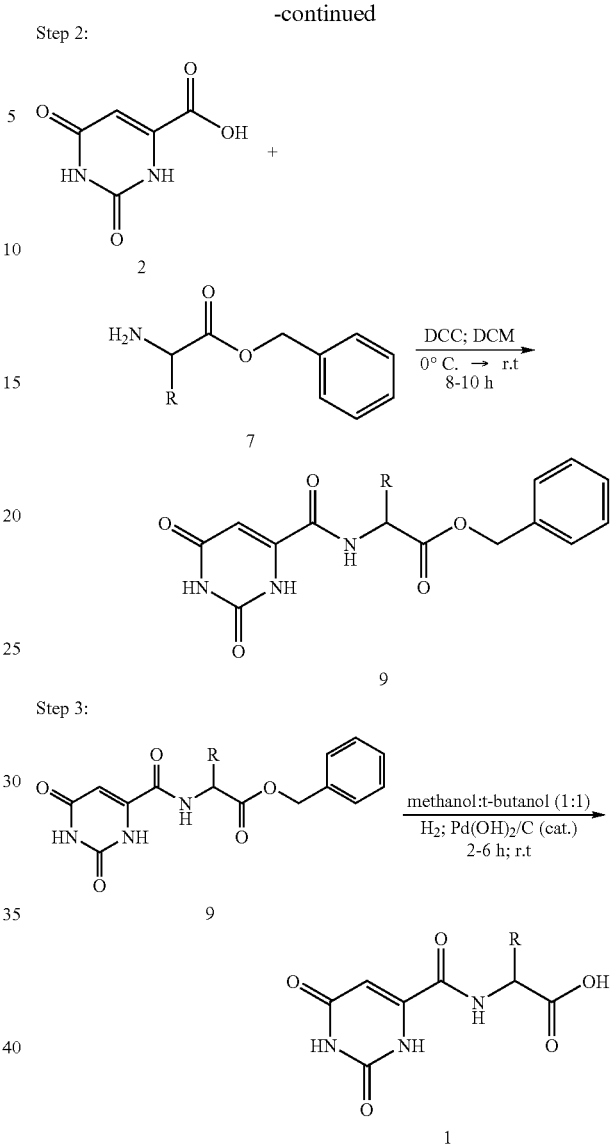

With reference to Scheme 2, in Step 1, an amino acid (5) is mixed with N,N'-diisolpropyl-O-benzylisourea (6) in the absence of solvent for about one hour, after which the volume of the reaction is increased by the addition of between about 200 and about 400 mL of dry tetrahydrofuran (THF). The reaction is then stirred at room temperature for between about 36 and about 48 hours to yield the benzyl protected amino acid (7) and the by by-product, diisopropylurea (8). The by-product is removed via vacuum filtration and the filtrate is then concentrated by the evaporation of the THF under reduced pressure. Further residual solvent can be removed by pumping the oil under high vacuum for about 24 hours. This protection is based upon that used by Mathias et al (Mathias L J, Fuller W D, Nissen D, Goodman M. Polydepsipeptides. 6. Synthesis of sequential polymers containing varying ratios of L-Alanine and L-Lactic acid. Macromolecules. May-June 1978; 11(3):534-9).

In various embodiments of the present invention, the amino acid (5) is selected from the group preferably consisting of Leucine, Valine, Isoleucine, Arginine and Phenylalanine. However any amino acid, as is known by one of skill in the art, may be utilized to synthesize an amino acid oratate amide according to the methods disclosed herein.

Step 2 describes the combining of the orotic acid (2) and the protected amino acid (7). The two substrates, 2 and 7, are stirred in DCM and submersed in an ice-water bath to bring the temperature of the reaction to about 0° C. After cooling, a solution of dicyclohexylcarbodiimine (DCC) and DCM is added to the mixture of 2 and 7 with vigorous stirring; the DCC acts to activate the carboxylic acid of the orotic acid in situ. Following the addition of the DCC the reaction is allowed to warm to room temperature with constant agitation. Stirring is maintained overnight (between about 8 and about 10 hours). The mixture is then filtered through Celite® in order to remove any by-products and unreacted materials. The filtrate is then concentrated under reduced pressure and purified by flash chromatography through a silica gel packed column to yield the benzyl protected amino acid orotate amide (9).

Step 3 describes the removal of the benzyl protecting group from the carboxylic acid of 9, via Palladium catalyzed hydrogenation. The benzyl protected amino acid orotate amide (9) is dissolved in a mixed solvent of methanol and tert-butanol in a 1:1 ratio. The catalyst, palladium hydroxide on carbon is added to the reaction, and the flask is then purged with hydrogen gas. The reaction is stirred at room temperature for between about 2 and about 6 hours, entirely under a hydrogen atmosphere. Once the reaction is complete the mixture is filtered through Celite® in order to remove the palladium and carbon. The filtrate is concentrated under reduced pressure and then purified by flash chromatography through a silica gel packed column to yield target amide compound, the amino acid orotate amide (1).

In various embodiments, according to the aforementioned, using the various amino acids, the following compounds are produced: 2-(2,6-dioxo-1,2,3,6-tetrahydropyrimidine-4-carboxamido)-4-methylpentanoic acid, 2-(2,6-dioxo-1,2,3,6-tetrahydropyrimidine-4-carboxamido)-3-methylbutanoic acid, 2-(2,6-dioxo-1,2,3,6-tetrahydropyrimidine-4-carboxamido)-3-methylpentanoic acid, 2-(2,6-dioxo-1,2,3,6-tetrahydropyrimidine-4-carboxamido)-4-guanidinopentanoic acid and 2-(2,6-dioxo-1,2,3,6-tetrahydropyrimidine-4-carboxamido)-3-phenylpropanoic acid.

The following examples illustrate specific amino acid orotate amides and routes of synthesis thereof. One of skill in the art may envision various other combinations within the scope of the present invention, considering examples with reference to the specification herein provided.

EXAMPLES BASED ON SCHEME 1

Example 1

2-(2,6-dioxo-1,2,3,6-tetrahydropyrimidine-4-carboxamido)-4-methylpentanoic acid

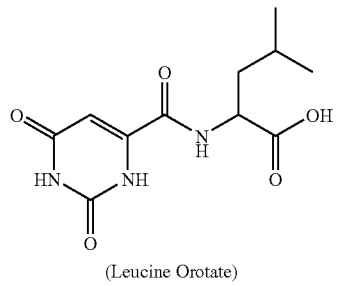

(Leucine Orotate)

In a dry 2-necked, round bottomed flask, equipped with a magnetic stirrer and fixed with a separatory funnel, containing 10.07 mL (130 mmol) of thionyl bromide, and a water condenser, is placed 15.61 g (100 mmol) of orotic acid. Addition of the thionyl bromide is completed with heating to about 45° C. over the course of about 80 minutes. When addition of the thionyl bromide is complete the mixture is heated and stirred for an additional hour. The water condenser is then replaced with a distillation side arm condenser and the crude mixture is distilled. The crude distillate in the receiving flask is then fractionally distilled to obtain the acyl bromide, 2,6-dioxo-1,2,3,6-tetrahydropyrimidine-4-carbonyl bromide (orotoyl bromide). This acyl bromide, 6.57 g (30 mmol), is put into a dry separatory funnel and combined with 25 mL of dry DCM for use in the next step of the reaction.

In a dry 3-necked, round bottomed flask, equipped with a magnetic stirrer, a thermometer, a nitrogen inlet tube and the dropping funnel containing the orotoyl bromide solution, 5.90 g (45 mmol) of Leucine is suspended, with stirring, in 50 mL of dry DCM. To this suspension a catalytic amount (~0.1 mmol) of DMAP is also added. The suspension is stirred in a dry ice and acetone bath to a temperature of about −15° C. When the target temperature is reached the drop wise addition of orotoyl bromide is commenced. Addition of orotoyl bromide continues, with constant cooling and stirring, until all of the orotoyl bromide is added, after which the reaction is allowed to warm to room temperature with constant agitation. The solution is then filtered to remove any remaining Leucine and the volatile DCM is removed from the filtrate under reduced pressure, the remainder is then purified by flash chromatography (ethyl acetate/hexanes; 1/5), yielding 2-(2,6-dioxo-1,2,3,6-tetrahydropyrimidine-4-carboxamido)-4-methylpentanoic acid.

Example 2

2-(2,6-dioxo-1,2,3,6-tetrahydropyrimidine-4-carboxamido)-3-methylbutanoic acid

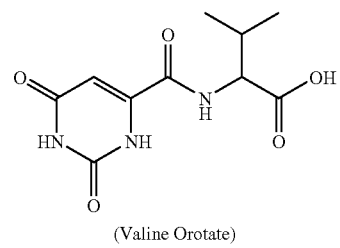

(Valine Orotate)

In a dry 2-necked, round bottomed flask, equipped with a magnetic stirrer and fixed with a separatory funnel, containing 13.13 ml (180 mmol) of thionyl chloride, and a water condenser, is placed 15.61 g (100 mmol) of orotic acid. Addition of the thionyl chloride is completed with heating to about 55° C. over the course of about 45 minutes. When addition of the thionyl chloride is complete the mixture is heated and stirred for an additional 45 minutes. The water condenser is then replaced with a distillation side arm condenser and the crude mixture is distilled. The crude distillate in the receiving flask is then fractionally distilled to obtain the acyl chloride, 2,6-dioxo-1,2,3,6-tetrahydropyrimidine-4-carbonyl chloride (orotoyl chloride). This acyl chloride, 6.11 g (35 mmol), is put into a dry separatory funnel and combined with 50 mL of dry DCM for use in the next step of the reaction.

In a dry 3-necked, round bottomed flask, equipped with a magnetic stirrer, a thermometer, a nitrogen inlet tube and the dropping funnel containing the orotoyl chloride solution, 6.56 g (56 mmol) of Valine is suspended, with stirring, in 50 mL of dry DCM. To this suspension a catalytic amount (~0.1 mmol) of DMAP is also added. The suspension is stirred in a dry ice and acetone bath to a temperature of about −15° C. When the target temperature is reached the drop wise addition of orotoyl chloride is commenced. Addition of orotoyl chloride continues, with constant cooling and stirring, until all of the orotoyl chloride is added, after which the reaction is allowed to warm to room temperature with constant agitation. The solution is then filtered to remove any remaining Valine and the volatile DCM is removed from the filtrate under reduced pressure, the remainder is then purified by flash chromatography (ethyl acetate/hexanes; 1/6), yielding 2-(2,6-dioxo-1,2,3,6-tetrahydropyrimidine-4-carboxamido)-3-methylbutanoic acid.

Example 3

2-(2,6-dioxo-1,2,3,6-tetrahydropyrimidine-4-carboxamido)-3-methylpentanoic acid

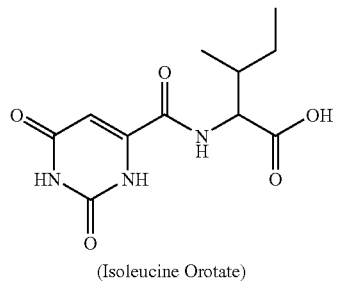

(Isoleucine Orotate)

In a dry 2-necked, round bottomed flask, equipped with a magnetic stirrer and fixed with a separatory funnel, containing 10.07 ml (130 mmol) of thionyl bromide, and a water condenser, is placed 15.61 g (100 mmol) of orotic acid. Addition of the thionyl bromide is completed with heating to about 30° C. over the course of about 130 minutes. When addition of the thionyl bromide is complete the mixture is heated and stirred for an additional hour. The water condenser is then replaced with a distillation side arm condenser and the crude mixture is distilled. The crude distillate in the receiving flask is then fractionally distilled to obtain the acyl bromide, orotoyl bromide. This acyl bromide, 10.95 g (50 mmol), is put into a dry separatory funnel and combined with 100 mL of dry DCM for use in the next step of the reaction.

In a dry 3-necked, round bottomed flask, equipped with a magnetic stirrer, a thermometer, a nitrogen inlet tube and the dropping funnel containing the orotoyl bromide solution, 9.84 g (75 mmol) of Isoleucine is suspended, with stirring, in 100 mL of dry DCM. To this suspension a catalytic amount (~0.1 mmol) of DMAP is also added. The suspension is stirred in a dry ice and acetone bath to a temperature of about −15° C. When the target temperature is reached the drop wise addition of orotoyl bromide is commenced. Addition of orotoyl bromide continues, with constant cooling and stirring, until all of the orotoyl bromide is added, after which the reaction is allowed to warm to room temperature with constant agitation. The solution is then filtered to remove any remaining Isoleucine and the volatile DCM is removed from the filtrate under reduced pressure, the remainder is then purified by flash chromatography (ethyl acetate/hexanes; 1/5), yielding 2-(2,6-dioxo-1,2,3,6-tetrahydropyrimidine-4-carboxamido)-3-methylpentanoic acid.

Thus while not wishing to be bound by theory, it is understood that reacting orotic acid or derivative thereof with an amino acid or derivative thereof to form an amide would have an enhanced stability in solution as compared to a related ester. Furthermore, it is understood that, dependent upon the specific amino acid, for example, BCAAs or derivatives thereof, employed in the foregoing synthesis, additional amino acid specific benefits, separate from the orotate substituent, will be conferred.

EXAMPLES BASED ON SCHEME 2

Example 4

2-(2,6-dioxo-1,2,3,6-tetrahydropyrimidine-4-carboxamido)-4-guanidinopentanoic acid

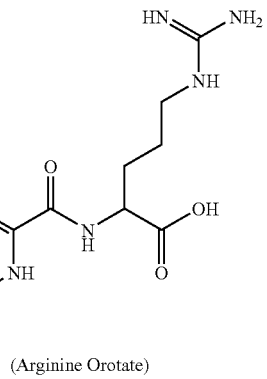

(Arginine Orotate)

In a dry round bottomed flask, equipped with a magnetic stirrer, 17.42 g (100 mmol) of Arginine is added to 23.43 g (100 mmol) of the oil, N,N'-diisopropyl-O-benzylisourea and stirred at room temperature for about one hour. After about one hour, the volume of the reaction is increased by the addition of 300 mL of dry tetrahyrdofuran (THF), and stirred at room temperature for an additional 36 hours. The resultant mixture is then filtered in order to remove the by-product, diisopropylurea, and the THF is then evaporated from the filtrate at reduced pressure. The oil which remains is pumped under high vacuum for about 24 hours yielding the protected amino acid, benzyl 2-amino-5-guanidinopentanoate, in pure enough form for subsequent steps.

A dry, 2-necked round bottomed flask, equipped with a magnetic stirrer and a dropping funnel containing a solution of 10.83 g (52.5 mmol) of N,N'-dicyclohexylcarbodiimide (DCC) dissolved in 60 mL of DCM, is charged with 7.80 g (50 mmol) of orotic acid, 14.54 g (55 mmol) of benzyl 2-amino-5-guanidinopentanoate, and 100 mL of DCM (all of which is under an argon atmosphere). The resultant mixture is stirred in an ice-water bath to cool the solution to a temperature of about 0° C. Following cooling, the solution of DCC from the dropping funnel is added and the reaction is allowed to warm to room temperature and then to stir overnight. The mixture is then filtered through a Celite® plug and the filtrate is purified by flash chromatography (ethyl acetate/hexanes; 1/3) to yield the benzyl protected orotate amino acid amide, benzyl 2-(2,6-dioxo-1,2,3,6-tetrahydropyrimidine-4-carboxamido)-5-guanidinopentanoate.

Lastly, in a single-necked round bottomed flask, 12.06 g (30 mmol) of the benzyl protected orotate amino acid amide is dissolved in 80 mL of a mixture of methanol and tert-butanol (1:1; molar). The catalyst Palladium hydroxide on carbon [Pd(OH)$_2$/C] is added to the mixture, the flask is then sealed with a septum, and purged with hydrogen gas. The reaction is then stirred for 3 hours under a hydrogen atmosphere, and then filtered through Celite®. The filtrate is then concentrated in vacuo and then purified by flash chromatography (ethyl acetate/hexanes; 1/5) to yield 2-(2,6-dioxo-1,2,3,6-tetrahydropyrimidine-4-carboxamido)-4-guanidinopentanoic acid.

Example 5

2-(2,6-dioxo-1,2,3,6-tetrahydropyrimidine-4-carboxamide)-3-phenylpropanoic acid

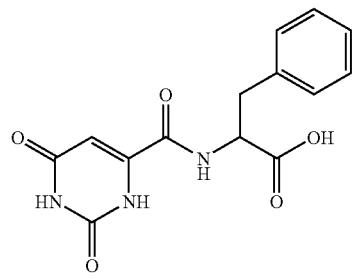

(Phenylalanine Orotate)

In a dry round bottomed flask, equipped with a magnetic stirrer, 13.22 g (80 mmol) of Phenylalanine is added to 18.75 g (80 mmol) of the oil, N,N'-diisopropyl-O-benzylisourea and stirred at room temperature for about one hour. After about one hour the volume of the reaction is increased by the addition of 350 mL of dry tetrahyrdofuran (THF), and stirred at room temperature for an additional 48 hours. The resultant mixture is then filtered in order to remove the by-product, diisopropylurea, and the THF is then evaporated from the filtrate at reduced pressure. The oil which remains is pumped under high vacuum for about 24 hours yielding the protected amino acid, benzyl 2-amino-3-phenylpropanoate, in pure enough form for subsequent steps.

A dry, 2-necked round bottomed flask, equipped with a magnetic stirrer and a dropping funnel containing a solution of 10.83 g (52.5 mmol) of N,N'-dicyclohexylcarbodiimide (DCC) dissolved in 60 mL of DCM, is charged with 7.80 g (50 mmol) of orotic acid, 15.32 g (60 mmol) of benzyl 2-amino-3-phenylpropanoate, and 100 mL of DCM (all of which is under an argon atmosphere). The resultant mixture is stirred in an ice-water bath to cool the solution to a temperature of about 0° C. Following cooling the solution of DCC from the dropping funnel is added and the reaction is allowed to warm to room temperature and then to stir overnight. The mixture is then filtered through a Celite® plug and the filtrate is purified by flash chromatography (ethyl acetate/hexanes; 1/3) to yield the benzyl protected orotate amino acid amide, benzyl 2-(2,6-dioxo-1,2,3,6-tetrahydropyrimidine-4-carboxamido)-3-phenylpropanoate.

Lastly, in a single-necked round bottomed flask, 15.74 g (40 mmol) of the benzyl protected orotate amino acid amide is dissolved in 80 mL of a mixture of methanol and tert-butanol (1:1; molar). The catalyst Palladium hydroxide on carbon [Pd(OH)$_2$/C] is added to the mixture, the flask is then sealed with a septum, and purged with hydrogen gas. The reaction is then stirred for 5 hours under a hydrogen atmosphere, and then filtered through Celite®. The filtrate is then concentrated in vacuo and then purified by flash chromatography (ethyl acetate/hexanes; 1/5) to yield 2-(2,6-dioxo-1,2,3,6-tetrahydropyrimidine-4-carboxamide)-3-phenylpropanoic acid.

Extensions and Alternatives

In the foregoing specification, the invention has been described with a specific embodiment thereof; however, it will be evident that various modifications and changes may be made thereto without departing from the broader spirit and scope of the invention.

What is claimed:

1. A compound having the general structure:

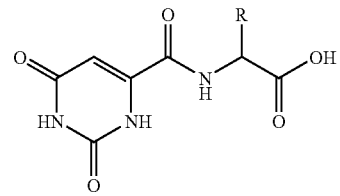

wherein R is selected from the group consisting of (CH$_3$)$_2$CHCH$_2$—; (CH$_3$)$_2$CH—; and CH$_3$CH$_2$CH(CH$_3$)—.

2. The compound of claim 1, wherein said compound is produced by a method comprising at least the steps of: mixing at least equivalent molar amounts of a thionyl halide with orotic acid to form an acyl halide; said acyl halide then being added to a dichloromethane suspension of an amino acid selected from the group consisting of being one of leucine, valine and isoleucine, in the presence of a 4-dimethyl-aminopyridine; and isolating and purifying the resulting compound of claim 1.

3. The compound of claim 2, wherein the halide of the thionyl halide is selected from the group consisting of fluorine, chlorine, bromine, and iodine.

4. The compound of claim 2, wherein the amino acid Leucine.

5. The compound of claim 2, wherein the 4-dimethyl-aminopyridine is present in catalytic amounts.

6. The compound of claim 2, wherein the acyl halide is produced at temperatures from between about 30° C. to about 55° C.

7. The compound of claim 2, wherein the acyl halide and the amino acid suspended in dichloromethane are reacted at temperatures from between about −15° C. to room temperature.

8. The compound of claim 2, wherein the amino acid orotate amide is isolated by filtration and then concentrated in vacuo.

9. The compound of claim 2, wherein the amino acid orotate amide is purified by flash chromatography using a silica gel packed column.

10. The compound of claim 2, wherein the amino acid orotate amide has the general structure of:

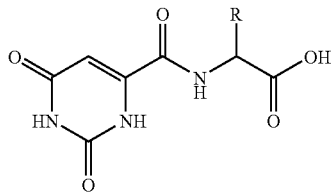

wherein R is (CH₃)₂ CHCH₂—.

11. The compound of claim 1, wherein said compound is produced by a method comprising at least the steps of: reacting an amino acid with N,N'-diisopropyl-O-benzylisourea to form a benzyl protected amino acid selected from the group consisting of leucine, valine and isoleucine; isolating said benzyl protected amino acid; reacting an activated orotic acid with the benzyl protected amino acid to form a benzyl protected amino acid orotate amide; isolating and purifying said benzyl protected amino acid orotate amide; removing the benzyl protecting group from said benzyl protected amino acid orotate amide; and isolating and purifying the deprotected compound of claim 1.

12. The compound of claim 11, wherein the amino acid Leucine.

13. The compound of claim 11, wherein the benzyl protected amino acid is isolated by filtration.

14. The compound of claim 11, wherein the orotic acid is activated in situ by dicyclohexylcarbodiimine.

15. The compound of claim 11, wherein the benzyl protected amino acid orotate amide is produced at temperatures from between about 0° C. to about room temperature.

16. The compound of claim 11, wherein the benzyl protected amino acid orotate amide is isolated by filtration through and then concentrated under reduced pressure.

17. The compound of claim 11, wherein the benzyl protected amino acid orotate amide is purified by flash chromatography using a silica gel packed column.

18. The compound of claim 11, wherein the benzyl protected amino acid orotate amide is deprotected by the removal of the benzyl group from the carboxylic acid.

19. The compound of claim 18, wherein the benzyl group from the carboxylic acid is removed via hydrogenation using a palladium on carbon catalyst.

20. The compound of claim 11, wherein the deprotected amino acid orotate amide is isolated by filtration and then concentrated under reduced pressure.

21. The compound of claim 11, wherein the deprotected amino acid orotate amide is purified by flash chromatography using a silica gel packed column.

22. The compound of claim 11, wherein the deprotected amino acid orotate amide has the general structure of:

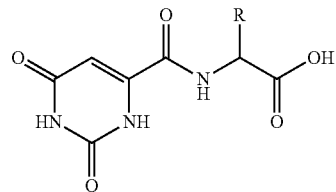

wherein R is (CH₃)₂ CHCH₂—.

* * * * *